(12) United States Patent
Schermeier et al.

(10) Patent No.: US 8,496,001 B2
(45) Date of Patent: Jul. 30, 2013

(54) PROCESS AND DEVICE FOR THE AUTOMATIC IDENTIFICATION OF BREATHING TUBES

(75) Inventors: Olaf Schermeier, Lübeck (DE); Heiko Lokotsch, Pokrent (DE); Axinja Schoenbeck, Klingberg (DE); Michael Wilkening, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 2202 days.

(21) Appl. No.: 11/381,662

(22) Filed: May 4, 2006

(65) Prior Publication Data
US 2006/0278221 A1 Dec. 14, 2006

(30) Foreign Application Priority Data
Jun. 8, 2005 (DE) .......................... 10 2005 026 561

(51) Int. Cl.
| A61M 16/00 | (2006.01) |
| A62B 9/00 | (2006.01) |
| A62B 27/00 | (2006.01) |
| G08B 3/00 | (2006.01) |
| G08B 5/00 | (2006.01) |

(52) U.S. Cl.
USPC ............. 128/202.22; 128/204.18; 128/204.21

(58) Field of Classification Search
USPC ............. 128/202.22, 203.12, 203.15, 204.22, 128/204.21, 200.24, 202.27, 203.14, 204.18, 128/205.23
See application file for complete search history.

(56) References Cited

U.S. PATENT DOCUMENTS

| 5,474,062 | A | * | 12/1995 | DeVires et al. | .......... | 128/205.24 |
| 5,534,851 | A | * | 7/1996 | Russek | ....................... | 340/573.4 |
| 6,126,610 | A | | 10/2000 | Rich et al. | | |
| 6,360,741 | B2 | * | 3/2002 | Truschel | .................. | 128/202.22 |
| 6,571,792 | B1 | * | 6/2003 | Hendrickson et al. | ... | 128/203.12 |
| 6,968,843 | B2 | * | 11/2005 | Kruger et al. | ............ | 128/204.21 |
| 2002/0144682 | A1 | | 10/2002 | Kruger et al. | | |
| 2003/0140921 | A1 | | 7/2003 | Smith et al. | | |
| 2004/0016431 | A1 | * | 1/2004 | Preveyraud | ............... | 128/204.18 |
| 2005/0061318 | A1 | * | 3/2005 | Faram | ..................... | 128/204.18 |
| 2005/0211761 | A1 | * | 9/2005 | Anttila et al. | ................. | 235/376 |
| 2006/0006999 | A1 | * | 1/2006 | Walczyk et al. | ......... | 340/539.27 |

FOREIGN PATENT DOCUMENTS

| DE | 201 13 789 U1 | 6/2002 |
| EP | 0 839 551 A2 | 5/1998 |
| EP | 1 188 457 A1 | 3/2002 |
| EP | 1 731 089 A1 | 12/2006 |
| WO | WO 00/61003 | 10/2000 |

* cited by examiner

*Primary Examiner* — Justine Yu
*Assistant Examiner* — Colin W Stuart
(74) *Attorney, Agent, or Firm* — McGlew and Tuttle, P.C.

(57) ABSTRACT

A process and a device/system are provided for the automatic identification of the type of a breathing tube. A memory element (5) is connected to the breathing tube (4). The memory element carries stored data identifying the breathing tube (4). The data are read by a reading unit (6), which is part of a respirator (1). The data may be read when the breathing tube (4) is brought into the vicinity of the respirator (1) or connected thereto.

24 Claims, 4 Drawing Sheets

PROCESS AND DEVICE FOR THE AUTOMATIC IDENTIFICATION OF BREATHING TUBES

CROSS REFERENCE TO RELATED APPLICATIONS

This application claims the benefit of priority under 35 U.S.C. §119 of German Patent Application DE 10 2005 026 561.8 filed Jun. 8, 2005, the entire contents of which are incorporated herein by reference.

FIELD OF THE INVENTION

The present invention pertains to a process and a device for the automatic identification of breathing tubes.

BACKGROUND OF THE INVENTION

Modern respiration systems are characterized by increasing complexity and diversity of possible uses. A plurality of components are frequently to be connected before a respiration system is ready for use. Different interfaces may be connected with such respiration systems, as a rule, with connection means, which may sometimes imply an increased risk for errors and possibly availability problems.

The connection of the breathing tube or the breathing tube system represents an essential connecting measure during the configuration of breathing systems. The breathing tube and the breathing tube system shall hereinafter be considered to be equivalent in connection with the present invention, because the particular fluidic design of the tubes and systems is not critical.

It is known, in principle, that the risk for misconnections can be reduced in medical engineering systems by connecting identification means to the individual components (DE 201 13 789 U1).

However, this has not hitherto been used in the area of breathing systems and breathing tubes because it was assumed that misconnections can be ruled out by the mechanical design of the connectors. However, the standards and types of breathing tubes that have meanwhile become established have led to a diversity that cannot be systematized exclusively by certain types of connectors. Each standard type of connector is now designed such that it can be connected to different breathing tube systems, which are intended for very special modes of respiration. However, this makes necessary the accurate identification of the type of the breathing tube system connected.

Various parameters, which are necessary for the optimal functionality of the device and are determined by the nature of the tube, have hitherto been measured for this purpose by the system and entered by the user in the software of the device. These include, for example, tube volumes or modes of heating.

SUMMARY OF THE INVENTION

The object of the present invention is to propose a possibility of reducing the risk for misconnections in breathing systems and of improving the ease of use without having to resort to a substantially increased effort.

According to the invention, a process is provided for the automatic identification of the type of a breathing tube. A memory element is connected to the breathing tube, on which data identifying the breathing tube are stored. The memory element is read by means of a reading unit which is part of a respirator (ventilator), when the breathing tube is brought into the vicinity of the respirator.

According to another aspect of the invention, a device is provided for the automatic recognition of the type of a breathing tube according to the process. At least one breathing tube is connected to a respirator with a memory element, on which data identifying the breathing tube are stored, is rigidly connected to the breathing tube. The respirator has means that make possible the reading of the data from the memory element when the breathing tube is located in the vicinity of the respirator.

The present invention is based essentially on the fact that when a breathing tube is connected to a respirator, connection elements will interact with one another, which require the relatively accurate positioning of an end of the breathing tube in relation to the respirator. This positioning is used to position a memory element, which is connected to the breathing tube and can be read by a reading unit, which is connected to the respirator. Data that make it possible to identify the type of the breathing tube are stored in the memory element.

The present invention consists of a process for the automatic identification of the type of a breathing tube, in which a memory element, which is connected to the breathing tube and on which data identifying the breathing tube are stored, is read by a reading unit that is part of the respirator, when the breathing tube is brought into the vicinity of the respirator.

The type of the breathing tube is advantageously identified by reading the memory element, which is connected to the breathing tube and on which data identifying the breathing tube are stored when the breathing tube is connected to the respirator. Misinterpretation due to the reading of other data storage media, which are located in the vicinity of the reading unit, are avoided as a result.

An alarm is advantageously triggered when a breathing tube that is not suitable for an intended mode of respiration is identified or a mode of respiration that does not fit the identified breathing tube is set on the respirator.

At the same time, a check can be performed to determine whether the breathing tube is connected correctly to the respirator, and an alarm is triggered when the breathing tube is not connected correctly to the respirator. Correct connection is defined in the sense of the present invention as the use of an intended breathing tube and the arrangement thereof in a functional manner. Incorrect positioning can be extensively ruled out as a result.

It is especially advantageous if the reading unit is designed as a writing and reading unit and additional data are stored in the memory element connected to the breathing tube while the breathing tube is being connected to the respirator. Possible additional data may be, for example, respiration parameters, patient data, accounting data, therapy data and/or diagnostic data as well as data that log the use of the breathing tube. These include data about cleaning and sterilization steps.

As a result, possibilities advantageously arise for keeping these additional data available for a later use. For example, after the breathing tube has been connected to a respirator, stored respiration parameters can be read and these respiration parameters can be taken over by the connected respirator, preferably after release by authorized personnel. The data may just as well be processed and passed on to a central system of the hospital's logistic unit or a patient management system.

One advantage of the present invention is that breathing tubes are frequently intended to remain in the vicinity of the patient for a rather long time in modern respiration systems, whereas the respirators proper are replaced more frequently or are connected to the patient for a short time only. Due to the connection, according to the present invention, of the data storage means with a breathing tube that remains in the vicinity of the patient for a longer period of time, loss of this data storage medium while the breathing tube is located in the vicinity of the patient is nearly ruled out. The breathing tube thus assumes the function of an always available, patient-related data storage unit in a manner according to the present invention. The connection of a data storage means with a breathing tube, which remains in the vicinity of the patient for a rather long time, is automatically linked with the fact that no additional actions are necessary for making available the data storage unit and this data on the data storage unit can never be forgotten.

The means for reading the data from the memory element are advantageously integrated in a pneumatic interface at the respirator and are designed such that reading takes place when a breathing tube compatible with this interface is connected. The connection means that can be connected to one another or the parts of the pneumatic interface that can be connected to one another are connected to the data transmission means at least in a sufficiently dimensionally stable manner in such a way that ensures that in case of the components connected to one another, namely, the breathing tube and the respirator, the data transmission means are arranged at least such that data transmission can take place. This principle of connecting data transmission means to position-determining connection means that can be connected to one another is to be considered to be integrated in the sense of the present invention.

Due to the integration of the data transmission means into the pneumatic interface, which must be connected for the operation of the respiration system anyway, it is achieved, furthermore, that no additional actions are necessary for connecting the data storage means at the breathing tube to a writing or reading unit, which is located at the respirator, which is highly advantageous for operation under pressure of time.

It is especially advantageous if the data transmission takes place in a contactless manner, which is especially advantageous when oxygen is handled.

In an advantageous embodiment of a system according to the present invention, the data storage means and/or the data transmission means are designed such that they are suitable for the storage and the transmission of additional information via breathing tubes that can be connected to the respirator. This information may contain, for example, data on manufacture, storage and shelf life.

In another advantageous embodiment, the data storage means and/or data transmission means are designed such that they are suitable for the storage and transmission of patient data, therapy data and/or diagnostic data. The data storage means can thus partially assume the function of an electronic patient file and make necessary data automatically available to the particular attending physician.

It proved to be particularly advantageous if the data transmission means and/or data storage means are part of an RFID system. The data storage means, in particular, comprises at least one memory element in the form of an RFID tag, which is rigidly connected to the breathing tube.

To prevent unauthorized access to the stored data, it is advantageous to code the data and to make them available only during reading by a corresponding decoding method. It is necessary for this that means for coding and decoding the transmitted and/or stored data be contained. These means may comprise, for example, suitable software components, which are integrated in a control unit of the respirator.

Furthermore, it is advantageous if means are contained that make it possible to manually store information that prevents the further use of the breathing tube connected to the respirator. These include, for example, a manual switch, which ensures the transmission and storage of a blocking code on actuation. If this code is subsequently read, the respirator will demand the replacement of the blocked breathing tube. This may be useful in case of unclear risks for infection or obvious damage.

The present invention will be explained in greater detail on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
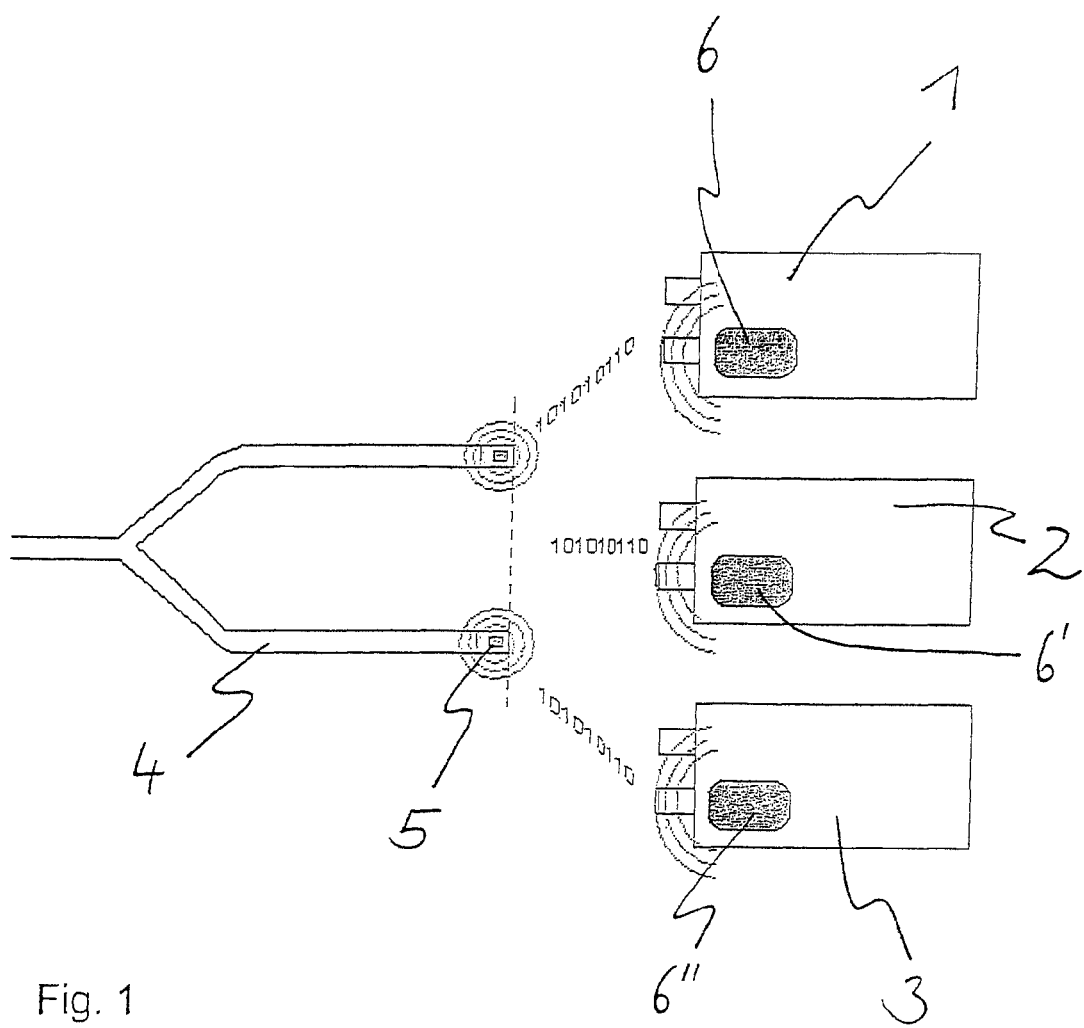
FIG. 1 is a schematic view showing a device for carrying out the process according to the present invention in the form of a respiration system.

Referring to the drawings in particular, a respiration system equipped according to the present invention comprises a breathing tube or a breathing tube system with a memory element. Furthermore, respirators are comprised, which have a reading and writing unit, which can communicate with the memory element when the breathing tube system is connected. Compared to conventional respiration systems, this offers numerous advantages, which will be described below.

There are a plurality of types of breathing tubes. Thus, there are disposable tubes and tubes that can be used several times, different tube lengths, different diameters, double tube systems, coaxial tubes, tubes with a semipermeable membrane for the passage of moisture, tubes heated by electric heating wires, and tubes with temperature sensors and flow-measuring units.

Many patients undergo mechanical respiration within the framework of their medical care, and different respiration systems may be used one after another in the course of the treatment.

Each combination of a given type of tube with a certain respirator requires defined respiration parameters and rules out other respiration parameters. In addition, respiration parameters must be selected according to therapeutic criteria. The essential parameters are the form of respiration, the oxygen content, the respiration rate, optionally the stroke volume, the maximum volume, the respiration pressure as well as a maximum allowable pressure.

Currently existing respiration systems make it necessary to set the patient's individual respiration parameters manually by the user on each respirator in order to ensure optimal treatment.

The optimal setting of the parameters depends on a large number of individual factors of the patient, which describe the respiration demand. The optimal setting of the respiration parameters therefore requires a considerable amount of time on the part of the attending staff.

After the beginning of the medical care, a patient usually passes through different stations. These may be an ambulance/helicopter, outpatient department, induction, OP, termination, intensive care unit and various transportations inside and outside the hospital. If respiration is required for a patient, the parameters must be set anew by the staff for each respiration system along this chain in conventional systems.

The effort described decreases and the risk for error is substantially diminished due to the use of a respiration system equipped according to the present invention. The type of the connected breathing tube is automatically identified.

Respiration parameters may be stored as data sets in the memory element, which is integrated in the breathing tube system. The breathing tube system remains at the patient when the clinical area or the respirator is changed. After connecting another respirator, these data are available for the newly connected respirator, which makes possible the automatic or semi-automatic setting of the necessary respiration parameters. Furthermore, it is possible to store data on forbidden parameters that must not be set by any means when the particular type of tube is used, which markedly reduces the risk for the incorrect supply of the patient. It is thus possible to embody at least an alarm device, which triggers an alarm when a breathing tube that is not suitable for an intended mode of respiration is identified or if a mode of respiration that does not fit the identified breathing tube is set on the respirator.

In addition or as an alternative to respiration parameters, data on a performed treatment can be stored in the memory element and later read for accounting purposes. For example, the minutes of respiration performed can thus be logged.

FIG. 1 shows a device for carrying out the process according to the present invention in the form of a respiration system. The exemplary embodiment pertains to a system comprising at least two respirators, and three respirators 1, 2, 3 in this case, and at least one breathing tube system 4, wherein the respirators are able to store and read individual respiration parameters of the patient on a memory element 5 on the breathing tube system 4 in a contactless manner when one of the respirators 1, 2, 3 is connected to the breathing tube system 4. In addition, data that make it possible to identify the type of the connected breathing tube system 4 are stored on the memory element 5. The respirators are an emergency respirator 1, an intensive care respirator 2 and an anesthesia respirator 3, as they may be used at a patient at different points in time.

The connection is established such that respiration parameters of one respirator are stored with a respective writing and reading unit 6, 6', 6'' on the memory element 5 of the breathing tube system 4 and these parameters are read by the other respirators from the memory element 5 in the breathing tube system 4 and can thus be set automatically or semi-automatically by the individual respirators. It is thus achieved that the respiration parameters set on the first respirator are also set on another respirator after the breathing tube system is plugged into that other respirator.

Basic requirements on breathing tubes are described in EN12342. This standard also defines the mechanical interface to the respiration system, which is usually designed by means of a conical male connector at the respiration system and a female connector at the breathing tube. The common standards of 22 mm, 15 mm and 10 mm diameter exist for the connectors. This connector system represents a pneumatic interface in the sense of the present invention, which ensures in the connected state the accurate positioning of the shaped parts that are in contact with one another.

Each respirator automatically stores all settings of the respiration parameters on the memory element in the breathing tube system. After the tube is plugged into another respirator, the latter will automatically read the particular data last stored on the memory element and sets these data on the new respirator. This may possibly take place after polling and confirmation on the display screen. If something has in turn changed in the settings in this respirator, this is automatically stored in the memory element and optionally transmitted to another respirator connected at a later point in time. In order not to change the process within the clinical procedure, a passive, cableless memory element is used, which can be read without additional working steps.

The advantage of the solution for the user is the marked simplification of the clinical processes and consequently the cost reduction due to fewer and shorter working steps.

The complicated manual individual programming of every individual respirator for a particular patient is eliminated and replaced by a brief polling. After a change in the clinical area or the respiration system, optimal respiration parameters can be set within a few seconds, whereas substantially more time is necessary for this in conventional systems.

Furthermore, optimal treatment of the patient is ensured in all areas, because errors in operating the system are extensively ruled out. A stable and lastingly optimized state of respiration can be achieved due to the continued use of optimized respiration parameters on different devices.

The communication between the breathing tube system and the particular respirator takes place via a contactless data connection in the exemplary embodiment.

The memory element is embodied by an RFID chip, a so-called tag, in the tube nozzle. This tag is applied either by bonding or injection. It is arranged geometrically in the tube nozzle such that it can be read and written on by a writing and reading unit in the respirator via an antenna when the breathing tube system is connected to the respirator.

The RFID embodies an inductive process, in which an antenna on a tag is excited with a defined frequency. A small chip on the RFID tag thereupon sends back the stored information. There are a large number of different RFID standards and RFID tags with different functionalities.

Figure 2:
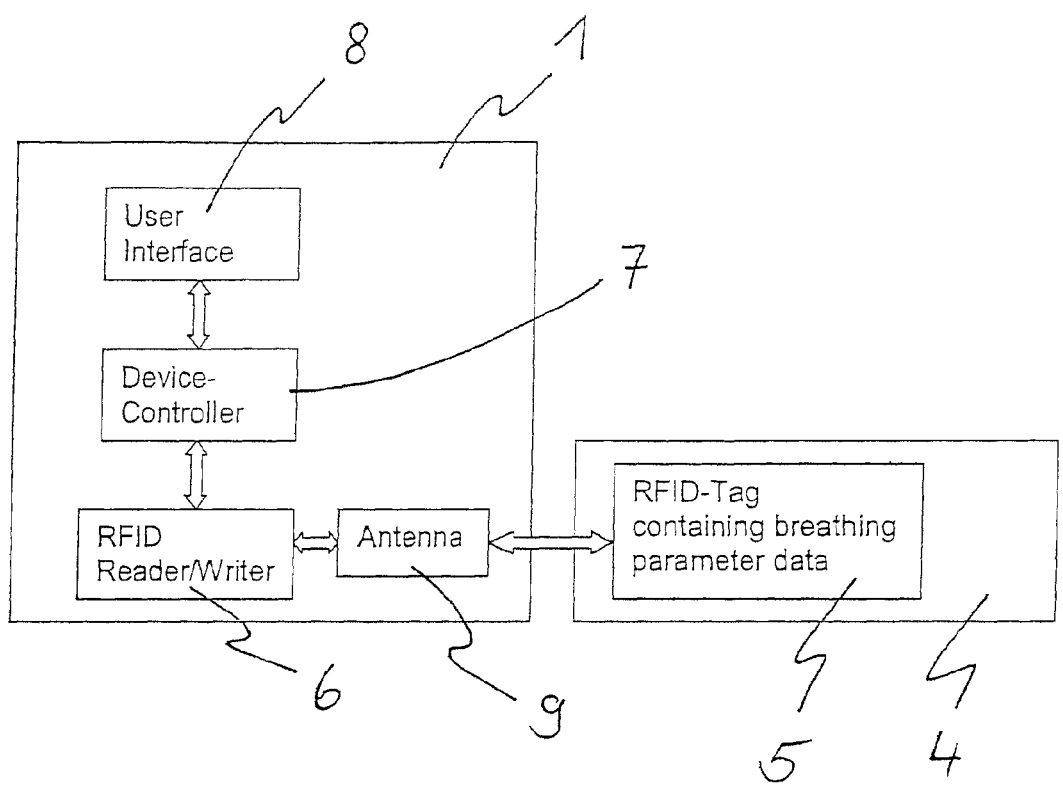
FIG. 2 is a block diagram of such a respiration system.

FIG. 2 shows a block diagram of a respiration system according to the present invention. The respirator 1 itself contains a control unit 7, which controls all the processes occurring during the operation of the device. Data necessary for this can be entered via an operating unit 8. The breathing tube system 4 that can be connected to the respirator 1 has an RFID tag as a memory element 5. A writing and reading unit 6 in the respirator 1 can communicate with this RFID tag, which is embodied via a corresponding antenna 9. The writing and reading unit 6 can also pass on the data read from the RFID tag to the control unit 7. If the RFID tag contains data on respiration parameters, these can replace entry via the operating unit. The respiration parameters are displayed, instead, on the operating unit 8 and taken over by the user as a setting by a release.

Various data, which identify the breathing tube system, are already written on the RFID tag in the state in which the breathing tube system is supplied. These data contain information in the form of an identification number, a manufacturer code and make it possible to read the date of manufacture and other specific data. Furthermore, respiration parameters, which must not be set with the breathing tube system, are stored. For example, large stroke volumes, which would be typical for the respiration of adult patients, can thus be prevented from being set on the respirator when a breathing tube system is used for newborns.

When the respirator recognizes the RFID tag, this means that a tube is connected. Respiration parameters that may already be stored on the RFID tag are subsequently compared with the respiration parameters set in the software of the device and stored on the RFID tag by the user in case of a change. Conversely, the stored respiration parameters are read from the RFID tag by means of the writing and reading unit after the breathing tube system is connected to a respirator and are used by an associated control device to automatically or semi-automatically, after release, set the mode of respiration, which is usually performed by a software of the device.

Figure 3:
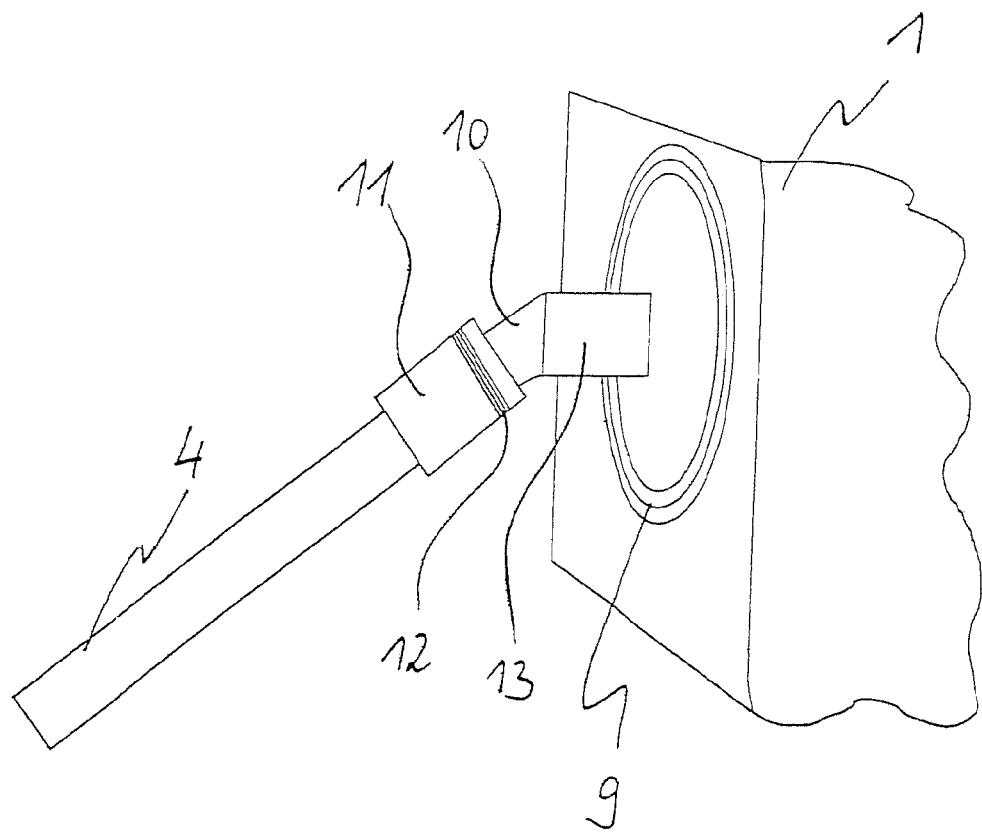
FIG. 3 is a schematic view showing a respiration system according to the present invention in the area of the pneumatic interface, i.e., the connection of the breathing tube to the respirator.

FIG. 3 shows a respiration system according to the present invention in the area of the pneumatic interface. A breathing gas connection with a variable-angle male connector 10 is arranged at a respirator 1. A breathing tube system 4 is connected to this connector 10 by connecting a sealing nozzle 11 as a female connector with the male connector 10. An RFID tag, not visible in this figure, is connected to an antenna 12. In this example, a coil is embedded as an antenna 12 of the tag by injection molding in the nozzle 11 such that its windings are directed at right angles to the axis of the tube connection. An antenna 9 of a device-side writing and reading unit is arranged in this variant at right angles to the axis of the part of the breathing gas connection 13 which is rigidly connected to the respirator 1. It is achieved in this manner that the fields that are formed around the antennas 9, 12 have a parallel component each in relation to the receiving antenna in all positions of the variable-angle male connector 10 (except a connector bent at right angles), which ensures a sufficient inductive coupling for carrying out the present invention.

Figure 4:
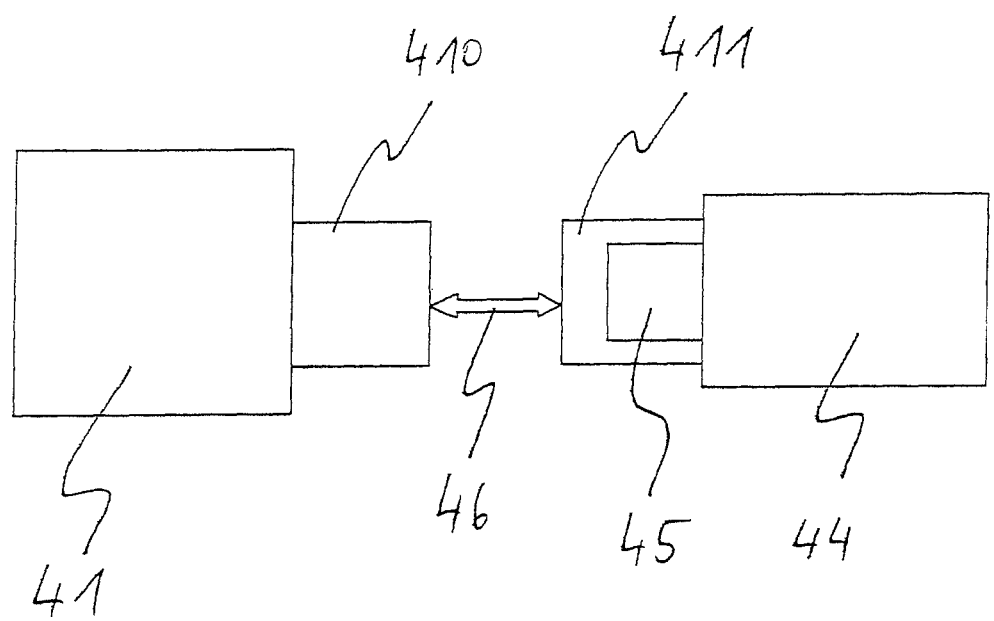
FIG. 4 is a schematic view showing the general design of a respiration system for carrying out the process according to the present invention.

FIG. 4 shows the general design of a respiration system for carrying out the process according to the present invention. It is a respiration system that comprises at least one breathing tube system 44 and a respirator 41, which can be connected to one another via positioning-determining connection means 410, 411, wherein the breathing tube system 44 contains at least one memory element 45, which can be read via an interface 46, which is mechanically connected to the position-determining connection means 410, 411.

While specific embodiments of the invention have been shown and described in detail to illustrate the application of the principles of the invention, it will be understood that the invention may be embodied otherwise without departing from such principles.

What is claimed is:

1. A process for the automatic identification of a type of a breathing tube, the process comprising:
    providing a respirator with a reading unit and a control unit for controlling respiration processes during operation of the device based on respiration parameter settings;
    providing a memory element connected to a breathing tube, the memory element having data identifying the breathing tube stored thereon;
    reading data from the memory element with the reading unit which is part of the respirator, when the breathing tube is brought into the vicinity of the respirator;
    identifying, with the control unit, when the breathing tube is not suitable for an intended mode of respiration, associated with the respiration parameter settings, or identifying a mode of respiration set at the respirator, associated with the respiration parameter settings, that does not fit the breathing tube set at the respirator; and
    triggering an alarm upon identifying when the breathing tube is not suitable for an intended mode of respiration or upon identifying a mode of respiration that does not fit the breathing tube set at the respirator.

2. A process for the automatic identification of the type of a breathing tube in accordance with claim 1, wherein the memory element is read when the breathing tube is operatively connected to the respirator.

3. A process in accordance with claim 1, further comprising:
    performing a check to determine whether the breathing tube is correctly connected to the respirator; and
    triggering an alarm if the breathing tube is not connected correctly to the respirator.

4. A process in accordance with claim 1, wherein the reading unit includes a writing and reading unit and further comprising:
    writing additional data, with the writing and reading unit, to the memory unit to store additional data in the memory element connected to the breathing tube while the breathing tube is connected to the respirator.

5. A process in accordance with claim 4, wherein respiration parameters are stored as additional data.

6. A process in accordance with claim 4, wherein at least one or more of patient data, accounting data, therapy data, diagnostic data and data that log the use of the breathing tube are stored as additional data.

7. A process in accordance with claim 4, wherein stored respiration parameters are read from the memory unit and said respiration parameters are passed by said memory unit to said control unit of said respirator and are taken over by said control unit as respiration parameters settings of the respirator upon connection of the breathing tube to the respirator.

8. A process in accordance with claim 4, further comprising:
    providing a central hospital logistics unit or a patient management system wherein stored data are read from the memory element and these data are processed and passed on to the central system of the hospital logistics unit or to the patient management system.

9. A process in accordance with claim 7, further comprising:
    providing an additional respiration device with an additional respiration device reading unit and an additional respiration device control unit for controlling respiration processes during operation of the additional respiration device based on respiration parameter settings; and
    reading stored respiration parameters from the memory unit with the additional respiration device reading unit and said respiration parameters are passed by said memory unit to said additional respiration device control unit and said passed respiration parameters are adopted by the additional respiration device control unit as respiration settings upon connection of the breathing tube to the additional respiration device.

10. A respirator system for the automatic recognition of the type of a breathing tube, the system comprising:
    a respirator;
    a breathing tube which can be connected to said respirator;
    a memory element having stored thereon data identifying said breathing tube, said memory element being rigidly connected to said breathing tube;

a memory element reading unit for reading of data from the memory element when the breathing tube is located in the vicinity of the respirator;

an alarm means for providing an alarm notification; and a control means for receiving data from said memory element reading unit and recognizing the type of breathing tube identified from said data and at least one of controlling respiration processes occurring during the operation of the device based on respiration parameters set on the respirator after determination that the breathing tube identified from said data is suitable for the respiration parameters set, and controlling respiration processes occurring during the operation of the device based on respiration parameters set on the respirator after an automatic adaptation of the mode of respiration based on setting respiration parameters of the respirator to a type suitable for the breathing tube identified from said data, activating the alarm after determination that the breathing tube identified from said data is not suitable for the respiration parameters set or if an automatic adaptation of the mode of respiration to the type of the breathing tube identified from said data is not possible, and deactivating the respirator after determination that the breathing tube identified from said data is not suitable for the respiration parameters set further use of the breathing tube.

11. A system in accordance with claim 10, wherein said memory element reading unit is integrated in a pneumatic interface at the respirator and is designed such that reading takes place when said breathing tube compatible with that interface is connected.

12. A system in accordance with claim 10, wherein the breathing tube memory element has data storage means, which can be read and written on upon being connected to said respirator.

13. A system in accordance with claim 10, further comprising connection means for determining whether the breathing tube is connected correctly to the respirator and which triggers an alarm when the breathing tube is not connected correctly to the respirator.

14. A system in accordance with claim 10, further comprising data transmission means associated with a data storage means of said memory element, said data transmission means associated with said data storage means comprising a radio frequency identification (RFID) system.

15. A system in accordance with claim 14, wherein said data transmission means and associated said data storage means of said memory element is an RFID tag rigidly connected to the breathing tube.

16. A system in accordance with claim 12, wherein said data storage means is for storing respiration parameters and said data storage means includes one of respiration parameters, which are to be set with the breathing tube system and, respiration parameters which must not be set with the breathing tube system, said control means comparing respiration parameters set on the respirator with respiration parameters stored on said data storage means of said automatic adaptation of the mode of respiration to the type of the breathing tube after the type of the breathing tube has been recognized.

17. A system in accordance with claim 12, wherein said data storage means is for storing patient data, accounting data, therapy data and/or diagnostic data.

18. A system in accordance with claim 10, wherein:
said respirator has a pneumatic interface between said respirator and said breathing tube;

said memory element reading unit and said memory element are associated with contactless transmission means for a contactless transmission of data between said respirator and said breathing tube, said contactless transmission means being integrated in the pneumatic interface between the respirator and the breathing tube.

19. A system in accordance with claim 10, wherein said memory element reading unit and said memory element are associated with means for coding and decoding data transmitted between said memory element reading unit and said memory element and/or stored data.

20. A system in accordance with claim 10, further comprising:

an additional respirator with an additional control means for receiving data from said memory element reading unit and recognizing the type of breathing tube identified from said data and an additional respirator memory element reading unit for reading stored respiration parameters from the memory element and passing the read respiration parameters to said control unit of said respirator, said additional control means and taking these respiration parameters over for operation of the additional respirator upon connection of the breathing tube to the additional respirator.

21. A process for a respirator and breathing tube, the process comprising:

providing a plurality of respirators each with a reading unit and a control unit for controlling respiration processes during operation of the device based on respiration parameter settings;

providing a memory element rigidly connected to a breathing tube, the memory element having data identifying the breathing tube stored thereon including at least one of respiration parameters, which are to be set with the breathing tube, and respiration parameters, which must not be set with the breathing tube;

reading data from the memory element with the reading unit which is part of the first to be used respirator of said plurality of respirators, when the breathing tube is brought into the vicinity of the first to be used respirator of said plurality of respirators;

passing the data from the reading unit to the control unit of the first to be used respirator of said plurality of respirators;

connecting the breathing tube to the first to be used respirator of said plurality of respirators; and controlling the operation of the respirator with the control unit based on the data passed from the reading unit to use only respiration parameters, which are to be set with the breathing tube and to not use respiration parameters, which must not be set with the breathing tube.

22. A process for a respirator and breathing tube according to claim 21, the process further comprising:

disconnecting the breathing tube from the first to be used respirator of said plurality of respirators;

connecting the breathing tube to a subsequently to be used respirator of said plurality of respirators;

reading data from the memory element with the reading unit which is part of the subsequently to be used respirator of said plurality of respirators, when the breathing tube is brought into the vicinity of the subsequently to be used respirator of said plurality of respirators;

passing the data from the reading unit to the control unit of the subsequently to be used respirator of said plurality of respirators;

adopting the passed respiration parameters by the control unit of the subsequently to be used respirator of said plurality of respirators as respiration settings upon connection of the breathing tube to the subsequently to be used respirator of said plurality of respirators; and controlling the operation of the subsequently to be used respirator of said plurality of respirators with the control unit of the subsequently to be used respirator of said plurality of respirators based on adopting the passed respiration parameters.

23. A process for a respirator and breathing tube according to claim 22, the process further comprising:

providing the reading unit of the at least the first to be used respirator of said plurality of respirators as a writing and reading unit;

prior to connecting the breathing tube to the first to be used respirator of said plurality of respirators, entering operator set respiration parameters into the first to be used respirator of said plurality of respirators; and comparing the operator set respiration parameters with respiration parameters from data passed from the reading unit to the control unit of the first to be used respirator and changing the respiration parameters or adding respiration parameters by writing new data to the memory element.

24. A process for a respirator and breathing tube according to claim 23, the process further comprising:

upon comparing the operator set respiration parameters with respiration parameters from data passed from the reading unit identifying, with the control unit, when the breathing tube is not suitable for an intended mode of respiration, associated with the respiration parameter settings, or identifying a mode of respiration set at the respirator, associated with the respiration parameter settings, that does not fit the breathing tube set at the respirator; and triggering an alarm upon identifying when the breathing tube is not suitable for an intended mode of respiration or upon identifying a mode of respiration that does not fit the breathing tube set at the respirator.

* * * * *